US012559547B2

(12) United States Patent
Weiner et al.

(10) Patent No.: US 12,559,547 B2
(45) Date of Patent: Feb. 24, 2026

(54) MULTIVALENT DNA ANTIBODY CONSTRUCTS AND USE THEREOF

(71) Applicant: THE WISTAR INSTITUTE OF ANATOMY AND BIOLOGY, Philadelphia, PA (US)

(72) Inventors: David Weiner, Merion, PA (US); Ami Patel, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 794 days.

(21) Appl. No.: 17/631,691

(22) PCT Filed: Jul. 31, 2020

(86) PCT No.: PCT/US2020/044408
§ 371 (c)(1),
(2) Date: Jan. 31, 2022

(87) PCT Pub. No.: WO2021/022113
PCT Pub. Date: Feb. 4, 2021

(65) Prior Publication Data
US 2022/0275065 A1 Sep. 1, 2022

Related U.S. Application Data

(60) Provisional application No. 62/880,821, filed on Jul. 31, 2019.

(51) Int. Cl.
*C07K 16/12* (2006.01)
*A61K 9/00* (2006.01)
*A61K 31/711* (2006.01)
*C07K 16/1214* (2026.01)

(52) U.S. Cl.
CPC ........ *C07K 16/1214* (2013.01); *A61K 9/0019* (2013.01); *A61K 31/711* (2013.01); *C07K 2317/21* (2013.01); *C07K 2317/52* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 9,951,123 B2 * | 4/2018 | Hasegawa | A61K 31/436 |
| 10,400,038 B2 * | 9/2019 | Keyt | A61P 35/00 |
| 11,639,389 B2 * | 5/2023 | Keyt | C07K 16/2827 |
| | | | 424/135.1 |
| 2006/0104974 A1 | 5/2006 | Davis | |
| 2010/0172899 A1 | 7/2010 | Irie | |
| 2015/0344584 A1 | 12/2015 | Umaña | |
| 2016/0311892 A1 | 10/2016 | Hasegawa | |
| 2019/0153076 A1 * | 5/2019 | Weiner | C07K 16/468 |

FOREIGN PATENT DOCUMENTS

| | | | | |
|---|---|---|---|---|
| WO | 2017193101 | | 11/2017 | |
| WO | WO-2017193101 A1 * | 11/2017 | | A61K 31/407 |

OTHER PUBLICATIONS

Emiri Hiramoto; Akihisa Tsutsumi; Risa Suzuki; Shigeru Matsuoka; Satoko Arai; Masahide Kikkawa; Toru Miyazaki, "The IgM pentamer is an asymmetric pentagon with an open groove that binds the AIM protein", Science Advances, (Oct. 10, 2018), vol. 4, No. 10, p. eaau1199, XP055729532.

Horn et al., "Preclinical In Vitro and In Vivo Characterization of the Fully Human Monoclonal IgM Antibody KBPA101 Specific for Pseudomonas aeruginosa Serotype IATS-011," Antimicrob Agents Chemother. Jun. 2010; 54(6): 2338-2344.

Knirel et al., "Polysaccharide antigens of Pseudomonas aeruginosa," Crit Rev Microbiol. 1990;17(4):273-304.

* cited by examiner

*Primary Examiner* — Jana A Hines
*Assistant Examiner* — Khatol S Shahnan Shah
(74) *Attorney, Agent, or Firm* — Riverside Law LLP

(57) ABSTRACT

Disclosed herein are compositions for generating a synthetic antibody or synthetic multivalent antibody in a subject. Also disclosed are methods for generating a synthetic antibody or synthetic multivalent antibody in a subject by administering a composition including a recombinant nucleic acid sequence that encodes an antibody, a synthetic antibody, or a synthetic multivalent antibody to a subject. The disclosure also provides compositions and methods of preventing and/ or treating a bacterial infection in a subject using said antibody, synthetic antibody, or synthetic multivalent antibody.

4 Claims, 3 Drawing Sheets

Specification includes a Sequence Listing.

DMAb-IgM

SEQUENCE LISTING

```
<160> NUMBER OF SEQ ID NOS: 6

<210> SEQ ID NO 1
<211> LENGTH: 1791
<212> TYPE: DNA
<213> ORGANISM: Artificial Sequence
<220> FEATURE:
<223> OTHER INFORMATION: O11-PANBAC-HC-IGM-1 (Heavy Chain)

<400> SEQUENCE: 1
ggatccgccg ccaccatgga ctggacctgg agaatcctgt tcctggtggc agcagcaacc      60
ggaacacacg cagaggagca ggtggtggag agcggcggcg gctttgtgca gccaggcggc     120
tccctgaggc tgtcttgcgc agcaagcggc ttcacctta gccctactg gatgcactgg     180 gtgaggcagg cacctggcaa gggactggtg tgggtgtcca gaatcaactc tgacggcagc     240
acatactatg ccgattccgt gaagggccgg ttcaccatct ctcgggataa cgcccgcaat     300
acactgtatc tgcagatgaa tagcctgcgc gccgaggaca gccgtgta ctattgtgcc     360 agggatagat actatggacc agagatgtgg ggacaggga ccatggtgac agtgagctcc     420
ggcagcgcct ccgccccaac cctgttccca ctggtgagct gcgagaactc tcctagcgac     480
acaagctccg tggcagtggg atgtctggca caggacttcc tgccagattc tatcaccttt     540
agctggaagt acaagaacaa tagcgatatc tctagcacac ggggctttcc atccgtgctg     600
cgcggcggca agtatgcagc cacctcccag gtgctgctgc cttctaagga cgtgatgcag     660
ggcacagatg agcacgtggt gtgcaaggtg cagcaccca acggcaataa ggagaagaac     720
gtgccactgc ccgtgatcgc agagctgccc cctaaggtgt ccgtgttcgt gccacccagg     780
gacggcttct ttggcaatcc cagaaagtct aagctgatct gtcaggccac cggctttcc     840 cctcggcaga tccaggtgtc ttggctgagg gagggcaagc aagtgggctc cggagtgacc     900
acagatcagg tgcaggcaga ggcaaaggag tccggaccta ccacatacaa ggtgacctct     960
acactgacca tcaaggagag cgactggctg ggccagtcca tgttcacctg cagggtggat    1020
cacagaggcc tgacatttca gcagaatgcc tcctctatgt gcgtgccaga ccaggatacc    1080
gccatcaggg tgttcgccat ccctccaagc ttcgcctcca tctttctgac aaagagcacc    1140
aagctgacat gcctggtgac cgacctgacc acatatgatt ccgtgaccat ctcttggaca    1200
cggcagaacg gcgaggccgt gaagacacac accaacatct ccgagtctca ccccaatgcc    1260
accttctctg ccgtgggaga ggcaagcatc tgcgaggacg attggaattc cggcgagagg    1320
tttacatgta ccgtgacaca caccgacctg cctagcccac tgaagcagac catctccagg    1380
cctaagggcg tggccctgca cagaccagac gtgtacctgc tgccccctgc cagggagcag    1440
ctgaacctga gagtctgc cacaatcacc tgtctggtga ccggcttcag cccagccgac    1500
gtgtttgtgc agtggatgca gaggggacag ccactgtctc ctgagaagta cgtgacaagc    1560
```

-continued

```
gccccaatgc ctgagccaca ggcaccaggc cgctatttcg cacactctat cctgaccgtg      1620
agcgaggagg agtggaacac aggcgagaca tatacctgcg tggtggcaca cgaggccctg      1680
ccaaatcggg tgaccgagcg cacagtggac aagagcaccg gcaagcccac actgtacaat      1740
gtgagcctgg tcatgtccga taccgccggc acatgttatt gataactcga g             1791
```

<210> SEQ ID NO 2
<211> LENGTH: 588
<212> TYPE: PRT
<213> ORGANISM: Artificial Sequence
<220> FEATURE:
<223> OTHER INFORMATION: O11-PANBAC-HC-IGM-1 (Heavy Chain) - Amino Acid

<400> SEQUENCE: 2

```
Met Asp Trp Thr Trp Arg Ile Leu Phe Leu Val Ala Ala Ala Thr Gly
1               5                   10                  15

Thr His Ala Glu Glu Gln Val Val Glu Ser Gly Gly Gly Phe Val Gln
                20                  25                  30

Pro Gly Gly Ser Leu Arg Leu Ser Cys Ala Ala Ser Gly Phe Thr Phe
            35                  40                  45

Ser Pro Tyr Trp Met His Trp Val Arg Gln Ala Pro Gly Lys Gly Leu
        50                  55                  60

Val Trp Val Ser Arg Ile Asn Ser Asp Gly Ser Thr Tyr Tyr Ala Asp
65                  70                  75                  80

Ser Val Lys Gly Arg Phe Thr Ile Ser Arg Asp Asn Ala Arg Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Arg Tyr Tyr Gly Pro Glu Met Trp Gly Gln Gly
            115                 120                 125

Thr Met Val Thr Val Ser Ser Gly Ser Ala Ser Ala Pro Thr Leu Phe
        130                 135                 140

Pro Leu Val Ser Cys Glu Asn Ser Pro Ser Asp Thr Ser Ser Val Ala
145                 150                 155                 160

Val Gly Cys Leu Ala Gln Asp Phe Leu Pro Asp Ser Ile Thr Phe Ser
                165                 170                 175

Trp Lys Tyr Lys Asn Asn Ser Asp Ile Ser Ser Thr Arg Gly Phe Pro
            180                 185                 190

Ser Val Leu Arg Gly Gly Lys Tyr Ala Ala Thr Ser Gln Val Leu Leu
            195                 200                 205

Pro Ser Lys Asp Val Met Gln Gly Thr Asp Glu His Val Val Cys Lys
        210                 215                 220

Val Gln His Pro Asn Gly Asn Lys Glu Lys Asn Val Pro Leu Pro Val
225                 230                 235                 240

Ile Ala Glu Leu Pro Pro Lys Val Ser Val Phe Val Pro Pro Arg Asp
                245                 250                 255

Gly Phe Phe Gly Asn Pro Arg Lys Ser Lys Leu Ile Cys Gln Ala Thr
            260                 265                 270

Gly Phe Ser Pro Arg Gln Ile Gln Val Ser Trp Leu Arg Glu Gly Lys
        275                 280                 285

Gln Val Gly Ser Gly Val Thr Thr Asp Gln Val Gln Ala Glu Ala Lys
    290                 295                 300

Glu Ser Gly Pro Thr Thr Tyr Lys Val Thr Ser Thr Leu Thr Ile Lys
305                 310                 315                 320
```

```
Glu Ser Asp Trp Leu Gly Gln Ser Met Phe Thr Cys Arg Val Asp His
                325             330             335

Arg Gly Leu Thr Phe Gln Gln Asn Ala Ser Ser Met Cys Val Pro Asp
            340             345             350

Gln Asp Thr Ala Ile Arg Val Phe Ala Ile Pro Pro Ser Phe Ala Ser
        355             360             365

Ile Phe Leu Thr Lys Ser Thr Lys Leu Thr Cys Leu Val Thr Asp Leu
    370             375             380

Thr Thr Tyr Asp Ser Val Thr Ile Ser Trp Thr Arg Gln Asn Gly Glu
385             390             395             400

Ala Val Lys Thr His Thr Asn Ile Ser Glu Ser His Pro Asn Ala Thr
            405             410             415

Phe Ser Ala Val Gly Glu Ala Ser Ile Cys Glu Asp Asp Trp Asn Ser
            420             425             430

Gly Glu Arg Phe Thr Cys Thr Val Thr His Thr Asp Leu Pro Ser Pro
            435             440             445

Leu Lys Gln Thr Ile Ser Arg Pro Lys Gly Val Ala Leu His Arg Pro
    450             455             460

Asp Val Tyr Leu Leu Pro Pro Ala Arg Glu Gln Leu Asn Leu Arg Glu
465             470             475             480

Ser Ala Thr Ile Thr Cys Leu Val Thr Gly Phe Ser Pro Ala Asp Val
            485             490             495

Phe Val Gln Trp Met Gln Arg Gly Gln Pro Leu Ser Pro Glu Lys Tyr
            500             505             510

Val Thr Ser Ala Pro Met Pro Glu Pro Gln Ala Pro Gly Arg Tyr Phe
            515             520             525

Ala His Ser Ile Leu Thr Val Ser Glu Glu Glu Trp Asn Thr Gly Glu
        530             535             540

Thr Tyr Thr Cys Val Val Ala His Glu Ala Leu Pro Asn Arg Val Thr
545             550             555             560

Glu Arg Thr Val Asp Lys Ser Thr Gly Lys Pro Thr Leu Tyr Asn Val
            565             570             575

Ser Leu Val Met Ser Asp Thr Ala Gly Thr Cys Tyr
            580             585
```

<210> SEQ ID NO 3
<211> LENGTH: 724
<212> TYPE: DNA
<213> ORGANISM: Artificial Sequence
<220> FEATURE:
<223> OTHER INFORMATION: O11-PANBAC-HC-IGM-1 (Light Chain)

<400> SEQUENCE: 3

```
atggtgctgc agacccaggt gttcatcagc ctgctgctgt ggatctccgg cgcctacggc      60
gacgtggtca tgacacagag ccccctgtct ctgcctgtga ccctgggaca gccagcctct     120
atcagctgca ggagctccca gagcctggtg tactccgatg caacacata tctgaattgg      180 ttccagcaga ggccaggaca gtcccccagg agactgatct acaaggtgtc taaccgggac     240
agcggcgtgc ctgatcgctt ctccggctct ggcagcggaa ccgactttac actgaagatc     300
tctagggtgg aggccgagga tgtgggcgtg tactattgta tgcaggggaac ccactggcca    360 ctgaccttcg gcggcggcac caaggtggag atcaagcgta cagtggccgc ccccagcgtg     420
ttcatctttc acccagcga cgagcagctg aagtccggca ccgcctctgt ggtgtgcctg      480
ctgaacaatt tctaccctcg ggaggccaag gtgcagtgga aggtggataa cgccctgcag     540
```

-continued

```
tccggcaatt ctcaggagag cgtgaccgag caggactcca aggattctac atatagcctg      600
agctccaccc tgacactgag caaggccgac tacgagaagc acaaggtgta tgcctgtgag      660
gtcacccacc aggggctgtc aagtccagtc actaaaagtt tcaatagggg agaatgttga      720
taac                                                                   724
```

```
<210> SEQ ID NO 4
<211> LENGTH: 239
<212> TYPE: PRT
<213> ORGANISM: Artificial Sequence
<220> FEATURE:
<223> OTHER INFORMATION: O11-PANBAC-HC-IGM-1 (Light Chain) - Amino Acid

<400> SEQUENCE: 4

Met Val Leu Gln Thr Gln Val Phe Ile Ser Leu Leu Leu Trp Ile Ser
1               5                   10                  15

Gly Ala Tyr Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Tyr Ser Asp Gly Asn Thr Tyr Leu Asn Trp Phe Gln Gln Arg
    50                  55                  60

Pro Gly Gln Ser Pro Arg Arg Leu Ile Tyr Lys Val Ser Asn Arg Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Gly Thr His Trp Pro Leu Thr Phe Gly Gly Gly Thr Lys
            115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 5
<211> LENGTH: 477
<212> TYPE: DNA
<213> ORGANISM: Artificial Sequence
<220> FEATURE:
<223> OTHER INFORMATION: Human J-chain

<400> SEQUENCE: 5
atgaagaacc atctgctgtt ttggggagtg ctggctgtgt ttatcaaggc tgtccatgtc       60
aaggctcagg aagacgaacg cattgtcctg gtggacaaca gtgcaaatg tgctagaatc      120 acctcccgga tcattcgcag ctccgaggac cctaacgaag atatcgtgga gcgaaatatt      180
```

-continued

```
aggatcattg tcccactgaa caatcgggaa aatatttctg atcccaccag tcctctgagg     240
acaagattcg tgtaccacct gagtgacctg tgcaagaaat gtgatcccac agaggtggaa     300
ctggacaacc agatcgtcac cgcaacacag tcaaatattt gcgacgaaga tagcgccact     360
gagacctgct acacttatga taggaacaag tgttacaccg ccgtggtccc tctggtgtat     420
ggcggagaaa ctaaaatggt cgagacagcc ctgactccag acgcttgtta tcccgat       477
```

```
<210> SEQ ID NO 6
<211> LENGTH: 159
<212> TYPE: PRT
<213> ORGANISM: Artificial Sequence
<220> FEATURE:
<223> OTHER INFORMATION: Human J-chain - Amino Acid

<400> SEQUENCE: 6

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
                100                 105                 110

Ile Cys Asp Glu Asp Ser Ala Thr Glu Thr Cys Tyr Thr Tyr Asp Arg
            115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155
```

MULTIVALENT DNA ANTIBODY CONSTRUCTS AND USE THEREOF

CROSS-REFERENCE TO RELATED APPLICATIONS

This application is the U.S. national phase application filed under 35 U.S.C. § 371 claiming benefit to International Patent Application No. PCT/US2020/044408, filed on Jul. 31, 2020, which is entitled to priority to U.S. Application No. 62/880,821, filed Jul. 31, 2019, the disclosures of which are incorporated herein by reference in their entireties.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: 206194_0039_00US_SequenceListing.txt created on Jan. 26, 2022, and 14 KB in size, is hereby incorporated by reference.

TECHNICAL FIELD

The present invention relates to a composition comprising a recombinant nucleic acid sequence for generating one or more synthetic antibodies, synthetic multivalent antibodies, and functional fragments thereof, in vivo, and a method of preventing and/or treating a disease or disorder in a subject by administering said composition.

BACKGROUND

Multidrug-resistant (MDR) *Pseudomonas* spp. are among the most difficult pathogens to treat. Infections by *Pseudomonas* spp. are a leading cause of acute pneumonia and chronic lung infections in individuals with cystic fibrosis, and are the most common source of infections of burn wounds or other injuries where they can lead to septic mortality. *Pseudomonas* spp. are able to attach to the surfaces of medical devices, such as medical implants, catheters, and artificial joints and cause multiple problems, for example clogging a catheter or physically damaging an implant. *Pseudomonas*, as biofilm forming bacteria, are highly resistant to high levels of antibiotics. Currently, therapeutic antibodies are approved for treatment of multiple diseases. Unfortunately, manufacture and delivery of purified antibodies is cost-prohibitive. Furthermore, these antibody therapies must be re-administered weekly-to-monthly—a challenging consideration in treatment of chronic conditions, such as prevention or treatment of biofilm formation on a medical implant.

Thus there is need in the art for improved therapeutics that prevent and/or treat bacterial infections, such as *Pseudomonas aeruginosa* infection, and biofilm formation. The current invention satisfies this need.

SUMMARY

The present invention is directed to a nucleic acid molecule encoding one or more synthetic antibodies, wherein the nucleic acid molecule comprises at least one selected from the group consisting of a) a nucleotide sequence encoding a synthetic antibody; and b) a nucleotide sequence encoding a fragment of a synthetic antibody.

In some embodiments, the antibody is a monoclonal antibody, monofunctional antibody, bifunctional antibody, bispecific antibody, multivalent antibody, defucosylated antibody, non-focusylated antibody, immunoglobulin, or any combination thereof.

In one embodiment, the nucleic acid molecule encodes a fragment of a multivalent antibody. In one embodiment, the multivalent antibody is a pentameric IgM antibody that forms in vivo.

In one embodiment, the nucleic acid molecule encodes at least one of a heavy chain, a light chain and a small polypeptide joining (J) chain of a pentameric IgM antibody.

In one embodiment, the antibody is an anti-*Pseudomomas* antibody.

In some embodiments, the antibody binds to a *Pseudomonas* antigen. In one embodiment, the antigen is *Pseudomonas* O antigen lipopolysaccharide, *Pseudomonas* peptidoglycan, *Pseudomonas* type III secretion system family protein, *Pseudomonas* exopolysaccharide family proteins, *Pseudomonas* exozyme proteins, any fragment thereof, or any combination thereof.

In one embodiment, the nucleic acid molecule comprises a nucleotide sequence encoding a cleavage domain.

In one embodiment, the nucleic acid molecule comprises a nucleotide sequence encoding a modified variable heavy chain region of an antibody.

In one embodiment, the nucleic acid molecule comprises a nucleotide sequence encoding a modified Fc region of an antibody.

In one embodiment, the nucleic acid molecule comprises a nucleotide sequence encoding a modified variable heavy chain region of an antibody and a modified Fc region of an antibody.

In one embodiment, the nucleic acid molecule comprises a nucleotide sequence encoding a modified variable heavy chain region of an antibody and a second nucleotide sequence encoding a modified Fc region of an antibody.

In one embodiment, the nucleic acid molecule comprises a nucleotide sequence encoding a modified Fc region of an immunoglobulin.

In one embodiment, the nucleic acid molecule comprises a nucleotide sequence encoding a modified Fc region of an IgM.

In one embodiment, the nucleic acid molecule comprises a nucleotide sequence encoding one or more of a variable heavy chain region and a variable light chain region of a synthetic antibody.

In one embodiment, the nucleic acid molecule comprises a nucleotide sequence encoding one or more of a variable heavy chain region and a variable light chain region of anti-*Pseudomonas* antibody.

In one embodiment, the nucleic acid molecule comprises a nucleotide sequence encoding one or more sequences as set forth in SEQ ID NO:2 and SEQ ID NO: 4.

In one embodiment, the nucleic acid molecule further comprises a nucleotide sequence encoding a variable J-chain.

In one embodiment, the nucleic acid molecule comprises a nucleotide sequence encoding the amino acid sequence as set forth in SEQ ID NO:6.

In one embodiment, the nucleic acid molecule comprises: a) a nucleotide sequence having at least about 95% identity over an entire length of the nucleic acid sequence to a nucleic acid sequence selected from the group consisting of SEQ ID NO:1, and SEQ ID NO: 3; b) a nucleotide sequence selected from the group consisting of SEQ ID NO:1 and SEQ ID NO:3.

In one embodiment, the nucleotide sequence encodes a leader sequence. In one embodiment, the nucleic acid molecule comprises an expression vector.

The invention further provides a composition comprising any of the nucleic acid molecules described herein.

In one embodiment the composition comprises a pharmaceutically acceptable excipient.

The invention further relates to a method of preventing or treating a disease in a subject, the method comprising administering to the subject a nucleic acid molecule or a composition as described herein.

In one embodiment, the disease is a *Pseudomonas aeruginosa* infection.

In one embodiment, the method further comprises administering an antibiotic agent to the subject. In one embodiment, an antibiotic is administered less than 10 days after administration of the nucleic acid molecule or composition.

The invention also relates to a method of preventing or treating a biofilm formation in a subject, the method comprising administering to the subject a nucleic acid molecule or a composition as described herein.

In one embodiment the biofilm is a *Pseudomonas aeruginosa* biofilm.

In one embodiment, the method further comprises administering an antibiotic agent to the subject. In one embodiment an antibiotic is administered less than 10 days after administration of the nucleic acid molecule or composition.

The invention also provides a strategy for the improved generation of higher order IgM antibody in vivo. In one embodiment, the higher order IgM antibody exhibits enhanced properties.

BRIEF DESCRIPTION OF THE DRAWINGS

FIG. 4, comprising FIG. 4A depicts exemplary results of quantification of human IgM in mouse sera at multiple time points. FIG. 4B depicts exemplary results demonstrating binding of DMAb mouse sera to *Pseudomonas aeruginosa* serotype O11 whole bacteria. An anti-human IgM antibody conjugated to HRP (with minimal cross-reactivity to mouse and rat) was used as the detection antibody.

DETAILED DESCRIPTION

Figure 2:
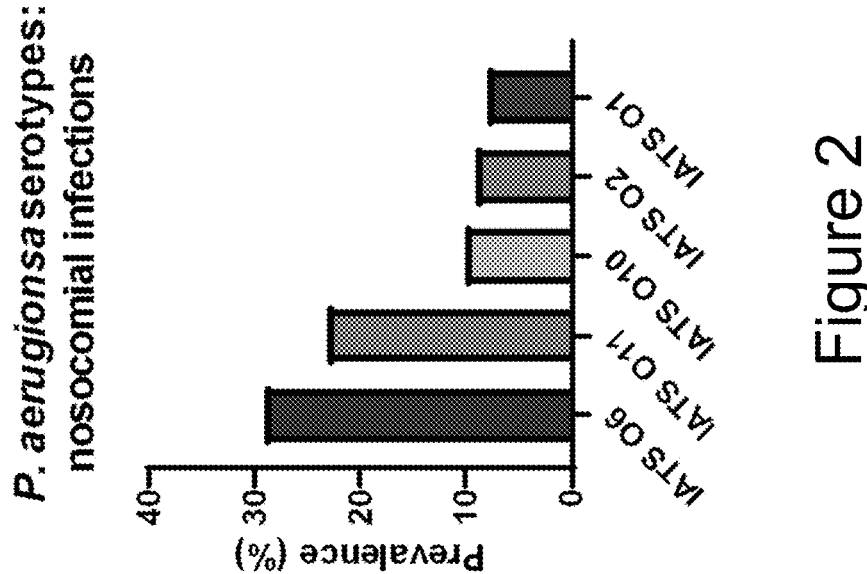
FIG. 2 depicts percent prevalence of IATS serotypes.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In one embodiment, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

In one embodiment, the heavy chain, light chain and J chain polypeptides expressed from the recombinant nucleic acid sequences can assemble into the synthetic IgM pentameric antibody. The heavy chain, light chain and J chain polypeptide can interact with one another such that assembly results in the synthetic IgM pentameric antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of" the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, a multivalent antibody, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is functional, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point $(T_m)$ for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Composition

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody, or a synthetic multivalent antibody, in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In some embodiments, the antibody is a monoclonal antibody, monofunctional antibody, bifunctional antibody, bispecific antibody, multivalent antibody, defucosylated antibody, non-focusylated antibody, high valency antibody, immunoglobulin, high valency immunoglobulin, or any combination thereof. In some embodiments, the antibody binds to bacteria, viruses, parasatises, fungal infections, and any combination thereof. In some embodiments, the high valency antibody binds to bacteria, viruses, parasatises, fungal infections, and any combination thereof. In some embodiments, the high valency immunoglobulin binds to bacteria, viruses, parasatises, fungal infections, and any combination thereof. In some embodiments, the immunoglobulin binds to bacteria, viruses, parasatises, fungal infections, and any combination thereof.

In one embodiment, the composition comprises a nucleotide sequence encoding a fragment of a synthetic multivalent antibody. In one embodiment, multivalent antibody forms in vivo after expression of the nucleotide sequence. In one embodiment, multivalent antibody has a modified (e.g., increased or decreased) level of complement activation with respect to a parental non-multivalent antibody. In one embodiment, the multivalent antibody is a trimeric antibody, a tetrameric antibody, a pentameric antibody, or a hexameric antibody. Therefore, in one embodiment, the invention provides nucleic acid molecules comprising a nucleotide sequence encoding a multivalent antibody or a fragment thereof.

In one embodiment, the multivalent antibody is a pentameric IgM antibody that forms in vivo. In one embodiment, the pentameric antibody of the invention comprises at least one light chain, at least one heavy chain and at least one J chain.

The multivalent antibody of the invention may be specific for any target or antigen, including, but not limited to a bacterial antigen, a viral antigen, and a self-antigen. In one embodiment, the multivalent antibody of the invention can be used to treat, prevent and/or protect against any disease, disorder, or condition associated with the target or antigen to which the multivalent antibody specifically binds, including, but not limited to, bacterial infection, viral infection and cancer.

In one embodiment, the nucleotide sequence comprises at least one codon optimized nucleotide sequences encoding the heavy chain, light chain and J chain of the pentameric IgM antibody.

In one embodiment, the nucleic acid molecule comprises a nucleotide sequence encoding a modified variable heavy chain region of an antibody. In one embodiment, the nucleic acid molecule comprises a nucleotide sequence encoding a modified Fc region of an antibody. In one embodiment, the nucleic acid molecule comprises a nucleotide sequence encoding a modified variable heavy chain region of an antibody and a modified Fc region of an antibody. In one embodiment, the nucleic acid molecule comprises a nucleotide sequence encoding a modified variable heavy chain region of an antibody and a second nucleotide sequence encoding a modified Fc region of an antibody. In one embodiment, the nucleic acid molecule comprises a nucleotide sequence encoding a modified Fc region of an immunoglobulin. In one embodiment, the nucleic acid molecule comprises a nucleotide sequence encoding a modified Fc region of an IgM.

In one embodiment, the nucleic acid molecule comprises a nucleotide sequence encoding an anti-*Pseudomonas* antibody.

In one embodiment, the nucleotide sequence encoding an anti-*Pseudomonas* antibody comprises codon optimized nucleic acid sequences encoding the variable VH and VL regions of an anti-*Pseudomonas* antibody. In one embodiment, the nucleotide sequence encoding a heavy chain of an optimized synthetic IgM pentameric anti-*Pseudomonas* antibody encodes SEQ ID NO:2, or a fragment or variant thereof. In one embodiment, the nucleotide sequence encoding a heavy chain of an optimized synthetic IgM pentameric anti-*Pseudomonas* antibody comprises SEQ ID NO:1, or a fragment or variant thereof.

In one embodiment, the nucleotide sequence encoding a light chain of an optimized synthetic IgM pentameric anti-*Pseudomonas* antibody encodes SEQ ID NO:4, or a fragment or variant thereof. In one embodiment, the nucleotide sequence encoding a light chain of an optimized synthetic IgM pentameric anti-*Pseudomonas* antibody comprises SEQ ID NO:3, or a fragment or variant thereof.

In one embodiment, the nucleotide sequence encoding a J chain of an optimized synthetic IgM pentameric anti-*Pseudomonas* antibody encodes SEQ ID NO:6, or a fragment or variant thereof. In one embodiment, the nucleotide sequence encoding a J chain of an optimized synthetic IgM pentameric anti-*Pseudomonas* antibody comprises SEQ ID NO:5, or a fragment or variant thereof.

In one embodiment, the nucleotide sequence encoding an anti-*Pseudomonas* antibody comprises one or more codon optimized nucleic acid sequences at least 90% homologous to SEQ ID NO:1 or a fragment of a nucleic acid sequence at least 90% homologous to SEQ ID NO:1. In one embodiment, the nucleotide sequence encoding an anti-*Pseudomonas* antibody comprises one or more codon optimized nucleic acid sequences as set forth in SEQ ID NO:1 or a fragment of a nucleic acid sequence as set forth in SEQ ID NO:1.

In one embodiment, the nucleotide sequence encoding an anti-*Pseudomonas* antibody comprises one or more RNA sequences transcribed from one or more DNA sequences at least 90% homologous to SEQ ID NO:1 or a fragment of a DNA sequence at least 90% homologous to SEQ ID NO:1. In one embodiment, the nucleotide sequence encoding an anti-*Pseudomonas* antibody comprises one or more RNA sequence transcribed from one or more DNA sequences as set forth in SEQ ID NO:1 or a fragment of a DNA sequence as set forth in SEQ ID NO:1.

In one embodiment, the nucleotide sequence encoding an anti-*Pseudomonas* antibody comprises one or more codon optimized nucleic acid sequences encoding an amino acid sequence at least 90% homologous to the amino acid sequence of SEQ ID NO:2, or a fragment of an amino acid sequence at least 90% homologous to the amino acid sequence of SEQ ID NO:2. In one embodiment, the nucleotide sequence encoding an anti-*Pseudomonas* antibody comprises one or more codon optimized nucleic acid sequences encoding the amino acid sequence of SEQ ID NO:2 or a fragment of the amino acid sequence of SEQ ID NO:2.

In one embodiment, the nucleotide sequence encoding an anti-*Pseudomonas* antibody comprises one or more RNA sequences transcribed from one or more DNA sequences encoding an amino acid sequence at least 90% homologous to SEQ ID NO:2 or a fragment of an amino acid sequence at least 90% homologous to SEQ ID NO:2. In one embodiment, the nucleotide sequence encoding an anti-*Pseudomonas* antibody comprises one or more RNA sequences transcribed from one or more DNA sequences encoding an amino acid sequence as set forth in SEQ ID NO:2 or a fragment of an amino acid sequence as set forth in SEQ ID NO:2.

In one embodiment, the nucleotide sequence encoding an anti-*Pseudomonas* antibody comprises one or more codon optimized nucleic acid sequences at least 90% homologous to SEQ ID NO:3 or a fragment of a nucleic acid sequence at least 90% homologous to SEQ ID NO:3. In one embodiment, the nucleotide sequence encoding an anti-*Pseudomonas* antibody comprises one or more codon optimized nucleic acid sequences as set forth in SEQ ID NO:3 or a fragment of a nucleic acid sequence as set forth in SEQ ID NO:3.

In one embodiment, the nucleotide sequence encoding an anti-*Pseudomonas* antibody comprises one or more RNA sequences transcribed from one or more DNA sequences at least 90% homologous to SEQ ID NO:3 or a fragment of a DNA sequence at least 90% homologous to SEQ ID NO:3. In one embodiment, the nucleotide sequence encoding an anti-*Pseudomonas* antibody comprises one or more RNA sequence transcribed from one or more DNA sequences as set forth in SEQ ID NO:3 or a fragment of a DNA sequence as set forth in SEQ ID NO:3.

In one embodiment, the nucleotide sequence encoding an anti-*Pseudomonas* antibody comprises one or more codon optimized nucleic acid sequences encoding an amino acid sequence at least 90% homologous to the amino acid sequence of SEQ ID NO:4, or a fragment of an amino acid sequence at least 90% homologous to the amino acid sequence of SEQ ID NO:4. In one embodiment, the nucleotide sequence encoding an anti-*Pseudomonas* antibody comprises one or more codon optimized nucleic acid sequences encoding the amino acid sequence of SEQ ID NO:4 or a fragment of the amino acid sequence of SEQ ID NO:4.

In one embodiment, the nucleotide sequence encoding an anti-*Pseudomonas* antibody comprises one or more RNA sequences transcribed from one or more DNA sequences encoding an amino acid sequence at least 90% homologous to SEQ ID NO:4 or a fragment of an amino acid sequence at least 90% homologous to SEQ ID NO:4. In one embodiment, the nucleotide sequence encoding an anti-*Pseudomonas* antibody comprises one or more RNA sequences transcribed from one or more DNA sequences encoding an amino acid sequence as set forth in SEQ ID NO:4 or a fragment of an amino acid sequence as set forth in SEQ ID NO:4.

In one embodiment, the nucleotide sequence encoding an anti-*Pseudomonas* antibody comprises one or more codon optimized nucleic acid sequences at least 90% homologous to SEQ ID NO:5 or a fragment of a nucleic acid sequence at least 90% homologous to SEQ ID NO:5. In one embodiment, the nucleotide sequence encoding an anti-*Pseudomonas* antibody comprises one or more codon optimized nucleic acid sequences as set forth in SEQ ID NO:5 or a fragment of a nucleic acid sequence as set forth in SEQ ID NO:5.

In one embodiment, the nucleotide sequence encoding an anti-*Pseudomonas* antibody comprises one or more RNA sequences transcribed from one or more DNA sequences at least 90% homologous to SEQ ID NO:5 or a fragment of a DNA sequence at least 90% homologous to SEQ ID NO:5. In one embodiment, the nucleotide sequence encoding an anti-*Pseudomonas* antibody comprises one or more RNA sequence transcribed from one or more DNA sequences as set forth in SEQ ID NO:5 or a fragment of a DNA sequence as set forth in SEQ ID NO:5.

In one embodiment, the nucleotide sequence encoding an anti-*Pseudomonas* antibody comprises one or more codon optimized nucleic acid sequences encoding an amino acid sequence at least 90% homologous to the amino acid sequence of SEQ ID NO:6, or a fragment of an amino acid sequence at least 90% homologous to the amino acid sequence of SEQ ID NO:6. In one embodiment, the nucleotide sequence encoding an anti-*Pseudomonas* antibody comprises one or more codon optimized nucleic acid sequences encoding the amino acid sequence of SEQ ID NO:6 or a fragment of the amino acid sequence of SEQ ID NO:6.

In one embodiment, the nucleotide sequence encoding an anti-*Pseudomonas* antibody comprises one or more RNA sequences transcribed from one or more DNA sequences encoding an amino acid sequence at least 90% homologous to SEQ ID NO:6 or a fragment of an amino acid sequence at least 90% homologous to SEQ ID NO:6. In one embodiment, the nucleotide sequence encoding an anti-*Pseudomonas* antibody comprises one or more RNA sequences transcribed from one or more DNA sequences encoding an amino acid sequence as set forth in SEQ ID NO:6 or a fragment of an amino acid sequence as set forth in SEQ ID NO:6.

In one embodiment, the invention relates to nucleic acid molecules encoding a fragment of an anti-*Pseudomonas* antibody. Fragments of an antibody include, but are not limited to, fragments comprising a single chain (e.g., a heavy chain, a light chain, or a J chain) of the antibody. In one embodiment, the fragment of an antibody may comprise a heavy chain fragment of an anti-*Pseudomonas* antibody. In one embodiment, a heavy chain fragment of an anti-*Pseudomonas* antibody comprises an amino acid sequence as set forth in SEQ ID NO:2. Therefore, in one embodiment, the nucleotide sequence encoding a fragment of an anti-*Pseudomonas* antibody comprises one or more codon optimized nucleic acid sequences encoding an amino acid sequence at least 90% homologous to the amino acid sequence of SEQ ID NO:2, or a fragment of an amino acid sequence at least 90% homologous to the amino acid sequence of SEQ ID NO:2. In one embodiment, the nucleotide sequence encoding an anti-*Pseudomonas* antibody comprises one or more codon optimized nucleic acid sequences encoding the amino acid sequence of SEQ ID NO:2 or a fragment of the amino acid sequence of SEQ ID NO:2.

In one embodiment, the nucleotide sequence encoding a fragment of an anti-*Pseudomonas* antibody comprises one or more RNA sequences transcribed from one or more DNA sequences encoding a fragment of an amino acid sequence at least 90% homologous to SEQ ID NO:2 or a fragment of an amino acid sequence at least 90% homologous to SEQ ID NO:2.

In one embodiment, the nucleotide sequence encoding a fragment of an anti-*Pseudomonas* antibody comprises one or more codon optimized nucleic acid sequences at least 90% homologous to SEQ ID NO:1 or a fragment of a nucleic acid sequence at least 90% homologous to SEQ ID NO:1. In one embodiment, the nucleotide sequence encoding an anti-*Pseudomonas* antibody comprises one or more codon optimized nucleic acid sequences as set forth in SEQ ID NO:1 or a fragment of a nucleic acid sequence as set forth in SEQ ID NO:1.

In one embodiment, the nucleotide sequence encoding a fragment of an anti-*Pseudomonas* antibody comprises one or more RNA sequences transcribed from one or more DNA sequences at least 90% homologous to SEQ ID NO:1 or a fragment of a DNA sequence at least 90% homologous to SEQ ID NO:1.

In one embodiment, the fragment of an antibody may comprise a light chain fragment of an anti-*Pseudomonas* antibody. In one embodiment, a light chain fragment of an anti-*Pseudomonas* antibody comprises an amino acid sequence as set forth in SEQ ID NO:4. Therefore, in one embodiment, the nucleotide sequence encoding a fragment of an anti-*Pseudomonas* antibody comprises one or more codon optimized nucleic acid sequences encoding an amino acid sequence at least 90% homologous to the amino acid sequence of SEQ ID NO:4, or a fragment of an amino acid sequence at least 90% homologous to the amino acid sequence of SEQ ID NO:4. In one embodiment, the nucleotide sequence encoding an anti-*Pseudomonas* antibody comprises one or more codon optimized nucleic acid sequences encoding the amino acid sequence of SEQ ID NO:4 or a fragment of the amino acid sequence of SEQ ID NO:4.

In one embodiment, the nucleotide sequence encoding a fragment of an anti-*Pseudomonas* antibody comprises one or more RNA sequences transcribed from one or more DNA sequences encoding a fragment of an amino acid sequence at least 90% homologous to SEQ ID NO:4 or a fragment of an amino acid sequence at least 90% homologous to SEQ ID NO:4.

In one embodiment, the nucleotide sequence encoding a fragment of an anti-*Pseudomonas* antibody comprises one or more codon optimized nucleic acid sequences at least 90% homologous to SEQ ID NO:3 or a fragment of a nucleic acid sequence at least 90% homologous to SEQ ID NO:3. In one embodiment, the nucleotide sequence encoding an anti-*Pseudomonas* antibody comprises one or more codon optimized nucleic acid sequences as set forth in SEQ ID NO:3 or a fragment of a nucleic acid sequence as set forth in SEQ ID NO:3.

In one embodiment, the nucleotide sequence encoding a fragment of an anti-*Pseudomonas* antibody comprises one or more RNA sequences transcribed from one or more DNA sequences at least 90% homologous to SEQ ID NO:3 or a fragment of a DNA sequence at least 90% homologous to SEQ ID NO:3.

In one embodiment, the fragment of an antibody may comprise a J chain fragment of an anti-*Pseudomonas* antibody. In one embodiment, a J chain fragment of an anti-*Pseudomonas* antibody comprises an amino acid sequence as set forth in SEQ ID NO:6. Therefore, in one embodiment, the nucleotide sequence encoding a fragment of an anti-*Pseudomonas* antibody comprises one or more codon optimized nucleic acid sequences encoding an amino acid sequence at least 90% homologous to the amino acid sequence of SEQ ID NO:6, or a fragment of an amino acid sequence at least 90% homologous to the amino acid sequence of SEQ ID NO:6. In one embodiment, the nucleotide sequence encoding an anti-*Pseudomonas* antibody comprises one or more codon optimized nucleic acid sequences encoding the amino acid sequence of SEQ ID NO:6 or a fragment of the amino acid sequence of SEQ ID NO:6.

In one embodiment, the nucleotide sequence encoding a fragment of an anti-*Pseudomonas* antibody comprises one or more RNA sequences transcribed from one or more DNA sequences encoding a fragment of an amino acid sequence at least 90% homologous to SEQ ID NO:6 or a fragment of an amino acid sequence at least 90% homologous to SEQ ID NO:6.

In one embodiment, the nucleotide sequence encoding a fragment of an anti-*Pseudomonas* antibody comprises one or more codon optimized nucleic acid sequences at least 90% homologous to SEQ ID NO:5 or a fragment of a nucleic acid sequence at least 90% homologous to SEQ ID NO:5. In one embodiment, the nucleotide sequence encoding an anti-*Pseudomonas* antibody comprises one or more codon optimized nucleic acid sequences as set forth in SEQ ID NO:5 or a fragment of a nucleic acid sequence as set forth in SEQ ID NO:5.

In one embodiment, the nucleotide sequence encoding a fragment of an anti-*Pseudomonas* antibody comprises one or more RNA sequences transcribed from one or more DNA sequences at least 90% homologous to SEQ ID NO:5 or a fragment of a DNA sequence at least 90% homologous to SEQ ID NO:5.

The composition of the invention can treat, prevent and/or protect against any disease, disorder, or condition associated with a bacterial activity. In certain embodiments, the composition can treat, prevent, and or/protect against bacterial infection. In certain embodiments, the composition can treat, prevent, and or/protect against bacterial biofilm formation. In certain embodiments, the composition can treat, prevent, and or/protect against *Pseudomonas aeruginosa* infection. In certain embodiments, the composition can treat, prevent, and or/protect against *Pseudomonas aeruginosa* biofilm formation. In certain embodiments, the composition can treat, prevent, and or/protect against sepsis.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. The synthetic antibody can provide at least about 50%, 55%, 60%, 65%, 70%, 75%, 80%, 85%, 90%, 95%, or 100% survival of the disease in the subject administered the composition. In other embodiments, the synthetic antibody can provide at least about 65%, 66%, 67%, 68%, 69%, 70%, 71%, 72%, 73%, 74%, 75%, 76%, 77%, 78%, 79%, or 80% survival of the disease in the subject administered the composition.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include at least one heterologous nucleic acid sequence or one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can include a heterologous nucleic acid sequence that encodes a J chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and a constant heavy chain region 4 (CH4), and/or a hinge region.

In some embodiments, the heavy chain polypeptide can include a VH region and a CH1 region. In other embodiments, the heavy chain polypeptide can include a VH region, a CH1 region, a hinge region, a CH2 region, a CH3 region, and a CH4 region.

The heavy chain polypeptide can include a complementarity determining region ("CDR") set. The CDR set can contain three or more hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) J Chain Polypeptide

The recombinant nucleic acid sequence construct can include the heterologous nucleic acid encoding the J chain polypeptide, a fragment thereof, a variant thereof, or a combination thereof.

(4) Protease Cleavage Site

The recombinant nucleic acid sequence construct can include the heterologous nucleic acid sequence encoding the protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(5) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(6) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(7) Intron

The recombinant nucleic acid sequence construct can include one or more introns. Each intron can include functional splice donor and acceptor sites. The intron can include an enhancer of splicing. The intron can include one or more signals required for efficient splicing.

(8) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(9) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(10) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(11) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, California).

(12) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, CH3, and CH4, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide. A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, CH3, and CH4, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, CH3, and CH4, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, California), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO:1 or SEQ ID NO: 3. In another embodiment, the nucleotide sequence comprises an RNA sequence transcribed by a DNA sequence encoding a polypeptide sequence at least 90% homologous to one of SEQ ID NO:2 or SEQ ID NO 4, or a variant thereof or a fragment thereof. Accordingly, in one embodiment, the invention provides an RNA molecule encoding one or more of the MAbs or DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585, 362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939, 792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. Antibody

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, a CH3 region, and CH4 region. The light chain polypeptide of the immunoglobulin can include a VL region and CL region.

The antibody can be a polyclonal or monoclonal antibody. The antibody can be a chimeric antibody, a single chain antibody, a multivalent antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

In one embodiment, the antibody naturally activated complement.

The antibody can be a modified antibody. For example, the antibody can be engineered through additions of scFv. In one embodiment, IgG can be engineered through additions of scFv.

In one aspect of the invention, the antibody can be a hexameric antibody. For example, in one embodiment, the antibody is a hexameric immunoglobulin. In one embodiment, the antibody is a hexameric IgM or IgG. In one embodiment, hexameric complex assembles during antigen target binding.

In one embodiment, the antibody can be modified to enhance complement activation. In one embodiment, the antibody can be modified to enhance pentamer or hexamer formation. For example, the modification of the antibody can lead to enhanced antibacterial activity, antifungal activity, antiviral activity, antiparasitic activity, and any combination thereof. In one embodiment, IgG Fc can be modified to enhance complement activation.

In one embodiment, the modification of the IgG Fc leads to enhanced antibacterial activity, antifungal activity, antiviral activity, antiparasitic activity, and any combination thereof. For example, in some embodiment, the antibody can be modified via a modification of I253, S254, Q311, A339, E345, D356, E382, Q386, E430, Y436, S440, or any combination thereof.

a. Multivalent Antibody

In one embodiment, the recombinant nucleic acid sequence can encode a multivalent antibody. Exemplary multivalent antibodies include, but are not limited to, triabodies, tetravalent antibodies, peptabodies and hexabodies. A triabody, tetravalent antibody, peptabody and hexabody comprise 3, 4, 5 and 6 variable domains, respectively. The multivalent antibody of the invention may comprise multiple identical variable domains targeting the same antigen or epitope, or alternatively may comprise multiple variable domains targeting two or more different antigens or epitopes.

In one embodiment, the recombinant nucleic acid sequence can encode a heavy chain or a light chain of an antibody comprising one or more mutations in the Fc region to support formation of a multi-valent antibody. For example, in one embodiment, the recombinant nucleic acid sequence can encode a heavy chain of an antibody comprising one or more mutation that enhances Fc:Fc interactions and hexamerization following surface-target binding and increases complement activation. Exemplary IgG Fc mutations that can support formation of multi-valent antibodies include, but are not limited to, mutations of one or more of residues Q311, A339, E430, E345, D356, I253, S254, Y436, Q386, E382, and S440. In one embodiment, a mutation to promote hexamer formation is E345K. In one embodiment, a mutation to promote hexamer formation is E430G. In one embodiment, a mutation to promote hexamer formation is S440Y.

In one embodiment, the recombinant nucleic acid sequence can encode a heavy chain, a light chain, or a J chain, or a combination thereof, of an IgM pentameric antibody. Immunoglobulin M (IgM) forms a predominantly pentameric complex that also contains a J chain. The IgM pentamer exhibits a variety of immune responses and plays a crucial role in defense against foreign pathogens and self-antigens. Monomeric IgM consists of 14 immunoglobulin domains (two sets of VH-CH1-CH2-CH3-CH4/VL-CL) in four polypeptide chains that form a pentameric component. The pentamer also contains an additional polypeptide, the J chain, which assembles the pentamer by firmly bridging the cysteine residues within the C-terminal region of two neighboring IgM monomers.

In one embodiment, the present invention provides a pentameric IgM antibody as described above which comprises a heavy chain, light chain and J chain of an anti-*Pseudomonas* antibody. In one embodiment, the pentameric IgM antibody comprises a heavy chain, light chain and J chain of an anti-O11 antibody.

b. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker. For example, a complex, non-natural bispecific antibody (e.g. IgG) can be derived using DMAbs.

In one embodiment, the bispecific antibody binds multiple epitopes. In one embodiment, the bispecific IgG binds multiple epitopes. In one embodiment, the bispecific antibody increase valency. In one embodiment, the bispecific IgG increase valency.

c. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

d. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

e. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

f. Reduced ADE Response

The antibody may be modified to reduce or prevent antibody-dependent enhancement (ADE) of disease associated with the antigen, but still neutralize the antigen.

5. Monoclonal Antibodies

In one embodiment, the invention provides anti-*Pseudomonas* antibodies. The antibodies may be intact monoclonal antibodies, and immunologically active fragments (e.g., a Fab or (Fab)$_2$ fragment), a monoclonal antibody heavy chain, or a monoclonal antibody light chain.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, a CH3 region, and a CH4 region. The light chain polypeptide of the immunoglobulin can include a VL region and CL region.

6. Antigen

The synthetic antibody or multivalent antibody of the invention is directed to an antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a bacterium. The antigen can be associated with bacterial infection. In one embodiment, the antigen can be a bacterial virulence factor. In one embodiment, the antigent can be associated with *Pseudomonas aeruginosa* infection.

In one embodiment, the antigen can be a lipooligosaccharide.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

Foreign Antigens

In some embodiments, the antigen is foreign. A foreign antigen is any non-self substance (i.e., originates external to the subject) that, when introduced into the body, is capable of stimulating an immune response.

a. Bacterial Antigens

The foreign antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthracis, methicillin*-resistant *Staphylococcus aureus* (MRSA), or *Clostridium difficile*. The bacterium can be *Pseudomonas aeruginosa*.

The foreign antigen can be a bacterial antigen or fragment or variant thereof. The bacterium can be a disease causing bacterium. The bacterium can be a *Pseudomonas aeruginosa*.

(a) *Pseudomonas aeruginosa* Antigens

The bacterial antigen may be a *Pseudomonas aeruginosa* antigen, or fragment thereof, or variant thereof. The *Pseudomonas aeruginosa* antigen can be from a virulence factor. Virulence factors associated with *Pseudomonas aeruginosa* include, but are not limited to structural components, enzymes and toxins. A *Pseudomonas aeruginosa* virulence factor can be one of exopolysaccharide, Adhesin, lipopolysaccharide, Pyocyanin, Exotoxin A, Exotoxin S, Cytotoxin, Elastase, Alkaline protease, Phospholipase C, Rhamnolipid, and components of a bacterial secretion system.

In one embodiment, an antigen is an extracellular polysaccharide (e.g. Alginate, Pel and Psl). In one embodiment, an antigen is one of polysaccharide synthesis locus (psi), a gene contained therein (e.g. pslA, pslB, pslC, pslD, pslE, pslF, pslG, pslH, pslI, pslJ, pslK, pslL, pslM, pslN and pslO), a protein or enzyme encoded therein (e.g. a glycosyl transferase, phosphomannose isomerase/GDP-D-mannose pyrophosphorylase, a transporter, a hydrolase, a polymerase, an acetylase, a dehydrogenase and a topoisomerase) or a product produced therefrom (e.g. Psl exopolysaccharide, referred to as "Psl").

In one embodiment, an antigen is a component of a bacterial secretion system. Six different classes of secretion systems (types I through VI) have been described in bacteria, five of which (types I, II, II, V and VI) are found in gram negative bacteria, including *Pseudomonas aeruginosa*. In one embodiment, an antigen is one of a gene (e.g. an apr or has gene) or protein (e.g. AprD, AprE, AprF, HasD, HasE, HasF and HasR) or a secreted protein (e.g. AprA, AprX and HasAp) of a type I secretion system. In one embodiment, an antigen is one of a gene (e.g. xcpA/pilD, xphA, xqhA, xcpP to Q and xcpR to Z) or protein (e.g. GspC to M, GspAB, GspN, GspO, GspS, XcpT to XcpX, FppA,) or a secreted protein (e.g. LasB, LasA, PlcH, PlcN, PlcB, CbpD, ToxA, PmpA, PrpL, LipA, LipC, PhoA, PsAP, LapA) of a type II secretion system. In one embodiment, an antigen is one of a gene (e.g. a psc, per, pop or exs gene) or protein (e.g. PscC, PscE to PscF, PscJ, PscN, PscP, PscW, PopB, PopD, PcrH and *Pseudomonas*) or a secreted protein (e.g. ExoS, ExoT, ExoU and ExoY) of a type III secretion system. In one embodiment, an antigen is a regulator of a type III secretion system (e.g. ExsA and ExsC). In one embodiment, an antigen is one of a gene (e.g. estA) or protein (e.g. EstA, CupB3, CupB5 and LepB) or a secreted protein (e.g. EstA, LepA, and CupB5) of a type V secretion system. In one embodiment, an antigen is one of a gene (e.g. a HSI-I, HSI-II and HSI-III gene) or protein (e.g. Fhal, ClpV1, a VgrG protein or a Hcp protein) or a secreted protein (e.g. Hcp1) of a type VI secretion system.

b. Viral Antigens

The foreign antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from human immunodeficiency virus (HIV), Chikungunya virus (CHIKV), dengue fever virus, papilloma viruses, for example, human papillomoa virus (HPV), polio virus, hepatitis viruses, for example, hepatitis A virus (HAV), hepatitis B virus (HBV), hepatitis C virus (HCV), hepatitis D virus (HDV), and hepatitis E virus (HEV), smallpox virus (Variola major and minor), vaccinia virus, influenza virus, rhinoviruses, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, lassa virus, arenavirus, or cancer causing virus.

c. Parasitic Antigens

The foreign antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing any one of the following diseases: Acanthamoeba keratitis, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be *Acanthamoeba, Anisakis, Ascaris lumbricoides, Botfly, Balantidium coli, Bedbug, Cestoda* (tapeworm), *Chiggers, Cochliomyia hominivorax, Entamoeba histolytica, Fasciola hepatica, Giardia lamblia, Hookworm, Leishmania, Linguatula serrata, Liver fluke, Loa loa, Paragonimus*—lung fluke, Pinworm, *Plasmodium falciparum, Schistosoma, Strongyloides stercoralis*, Mite, Tapeworm, *Toxoplasma gondii, Trypanosoma*, Whipworm, or *Wuchereria bancrofti*.

d. Fungal Antigens

The foreign antigen can be a fungal antigen or fragment or variant thereof. The fungus can be *Aspergillus* species, *Blastomyces dermatitidis, Candida* yeasts (e.g., *Candida albicans*), *Coccidioides, Cryptococcus neoformans, Cryptococcus gattii, dermatophyte, Fusarium species, Histoplasma capsulatum, Mucoromycotina, Pneumocystis jirovecii, Sporothrix schenckii, Exserohilum*, or *Cladosporium*.

e. Self Antigens

In some embodiments, the antigen is a self antigen. A self antigen may be a constituent of the subject's own body that is capable of stimulating an immune response. In some embodiments, a self antigen does not provoke an immune response unless the subject is in a disease state, e.g., an autoimmune disease.

Self antigens may include, but are not limited to, cytokines, antibodies against viruses such as those listed above including HIV and Dengue, antigens affecting cancer progression or development, and cell surface receptors or transmembrane proteins.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

Illustrative examples of a tumor associated surface antigen are CD10, CD19, CD20, CD22, CD33, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, CD133, IL3R, fibroblast activating protein (FAP), CDCP1, Derlin1, Tenascin, frizzled 1-10, the vascular antigens VEGFR2 (KDR/FLK1), VEGFR3 (FLT4, CD309), PDGFR-α (CD140a), PDGFR-.beta. (CD140b) Endoglin, CLEC14, Tem1-8, and Tie2. Further examples may include A33, CAMPATH-1 (CDw52), Carcinoembryonic antigen (CEA), Carboanhydrase IX (MN/CA IX), CD21, CD25, CD30, CD34, CD37, CD44v6, CD45, CD133, de2-7 EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72. Examples of antigens expressed on the extracellular matrix of tumors are tenascin and the fibroblast activating protein (FAP).

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Aspects of the present invention include compositions for enhancing an immune response against an antigen in a subject in need thereof, comprising a synthetic multivalent antibody capable of generating an immune response in the subject, or a biologically functional fragment or variant thereof.

7. Excipients and Other Components of the Composition

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

8. Method of Generating the Synthetic Antibody

The present invention also relates a method of generating the synthetic antibody or synthetic multivalent antibody. The method can include administering the composition to the subject in need thereof by using the method of delivery described in more detail below. Accordingly, the synthetic antibody or synthetic multivalent antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

9. Method of Identifying or Screening for the Antibody

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

10. Method of Delivery of the Composition

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb.

5, 2008, drawn to method of injecting DNA are contemplated herein. The above-patents are incorporated by reference in their entirety.

11. Method of Treatment

Also provided herein is a method of treating, protecting against, and/or preventing disease in a subject in need thereof by generating the synthetic antibody or synthetic multivalent antibody in the subject. The method can include administering the composition to the subject. Administration of the composition to the subject can be done using the method of delivery described above.

In certain embodiments, the invention provides a method of treating protecting against, and/or preventing a disease or disorder associated with a target of the synthetic antibody or synthetic multivalent antibody. In various embodiments, the disease or disorder is a bacterial infection, a viral infection, a fungal infection, a disease or disorder associated with a parasite, or a disease or disorder associated with a self antigen, including, but not limited to, cancer.

In certain embodiments, the invention provides a method of treating protecting against, and/or preventing a bacterial infection. In one embodiment, the method treats, protects against, and/or prevents formation of a bacterial biofilm. In one embodiment, the method treats, protects against, and/or prevents *Pseudomonas aeruginosa* infection or biofilm formation. In one embodiment, the method treats, protects against, and/or prevents *Pseudomonas aeruginosa* infection of a wound.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. In one embodiment, the synthetic antibody can provide increased survival of the disease in the subject over the expected survival of a subject having the disease who has not been administered the synthetic antibody. In various embodiments, the synthetic antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the synthetic antibody can provide increased protection against the disease in the subject over the expected protection of a subject who has not been administered the synthetic antibody. In various embodiments, the synthetic antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The composition dose can be between 1 µg to 10 mg active component/kg body weight/time, and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

12. Use in Combination with Antibiotics

The present invention also provides a method of treating, protecting against, and/or preventing disease in a subject in need thereof by administering a combination of the synthetic antibody and a therapeutic antibiotic agent.

The synthetic antibody and an antibiotic agent may be administered using any suitable method such that a combination of the synthetic antibody and antibiotic agent are both present in the subject. In one embodiment, the method may comprise administration of a first composition comprising a synthetic antibody of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a synthetic antibody of the invention by any of the methods described in detail above and a second composition comprising an antibiotic agent concurrently. In one embodiment, the method may comprise administration of a first composition comprising a synthetic antibody of the invention by any of the methods described in detail above and a second composition comprising an antibiotic agent concurrently. In one embodiment, the method may comprise administration of a single composition comprising a synthetic antibody of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

13. Cancer Therapy

In one embodiment, the invention has multiple provides methods of treating or preventing cancer, or of treating and preventing growth or metastasis of tumors. Related aspects, illustrated of the invention provide methods of preventing, aiding in the prevention, and/or reducing metastasis of hyperplastic or tumor cells in an individual.

One aspect of the invention provides a method of inhibiting metastasis in an individual in need thereof, the method comprising administering to the individual an effective amount of a nucleic acid molecule encoding a multivalent antibody of the invention, wherein the multivalent antibody is specific for the cancer to be treated. The invention further provides a method of inhibiting metastasis in an individual in need thereof, the method comprising administering to the individual an effective metastasis-inhibiting amount of a nucleic acid molecule encoding a multivalent antibody of the invention, wherein the multivalent antibody is specific for the cancer to be treated.

In some embodiments of treating or preventing cancer, or of treating and preventing metastasis of tumors in an individual in need thereof, a second agent is administered to the individual, such as an antineoplastic agent. In some embodiments, the second agent comprises a second metastasis-inhibiting agent, such as a plasminogen antagonist, or an adenosine deaminase antagonist. In other embodiments, the second agent is an angiogenesis inhibiting agent.

The compositions of the invention can be used to prevent, abate, minimize, control, and/or lessen cancer in humans and animals. The compositions of the invention can also be used to slow the rate of primary tumor growth. The compositions of the invention when administered to a subject in need of treatment can be used to stop the spread of cancer cells. As such, an effective amount of a nucleic acid molecule encoding a multivalent antibody of the invention, wherein the multivalent antibody is specific for the cancer to be treated can be administered as part of a combination therapy with one or more drugs or other pharmaceutical agents. When used as part of the combination therapy, the decrease in metastasis and reduction in primary tumor growth afforded by the compositions of the invention allows for a more effective and efficient use of any pharmaceutical or drug therapy being used to treat the patient. In addition, control of metastasis by the compositions of the invention affords the subject a greater ability to concentrate the disease in one location.

In one embodiment, the invention provides methods for preventing metastasis of malignant tumors or other cancerous cells as well as to reduce the rate of tumor growth. The methods comprise administering an effective amount of a nucleic acid molecule encoding a multivalent antibody of the invention, wherein the multivalent antibody is specific for the cancer to be treated, to a subject diagnosed with a malignant tumor or cancerous cells or to a subject having a tumor or cancerous cells.

The following are non-limiting examples of cancers that can be treated by the methods and compositions of the invention: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer metastasis comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compounds of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the invention include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin;

ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

14. Generation of Synthetic Antibodies In Vitro and Ex Vivo

In one embodiment, the synthetic antibody or synthetic multivalent antibody is generated in vitro or ex vivo. For example, in one embodiment, a nucleic acid encoding a synthetic antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

The present invention has multiple aspects, illustrated by the following non-limiting examples.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Figure 1:
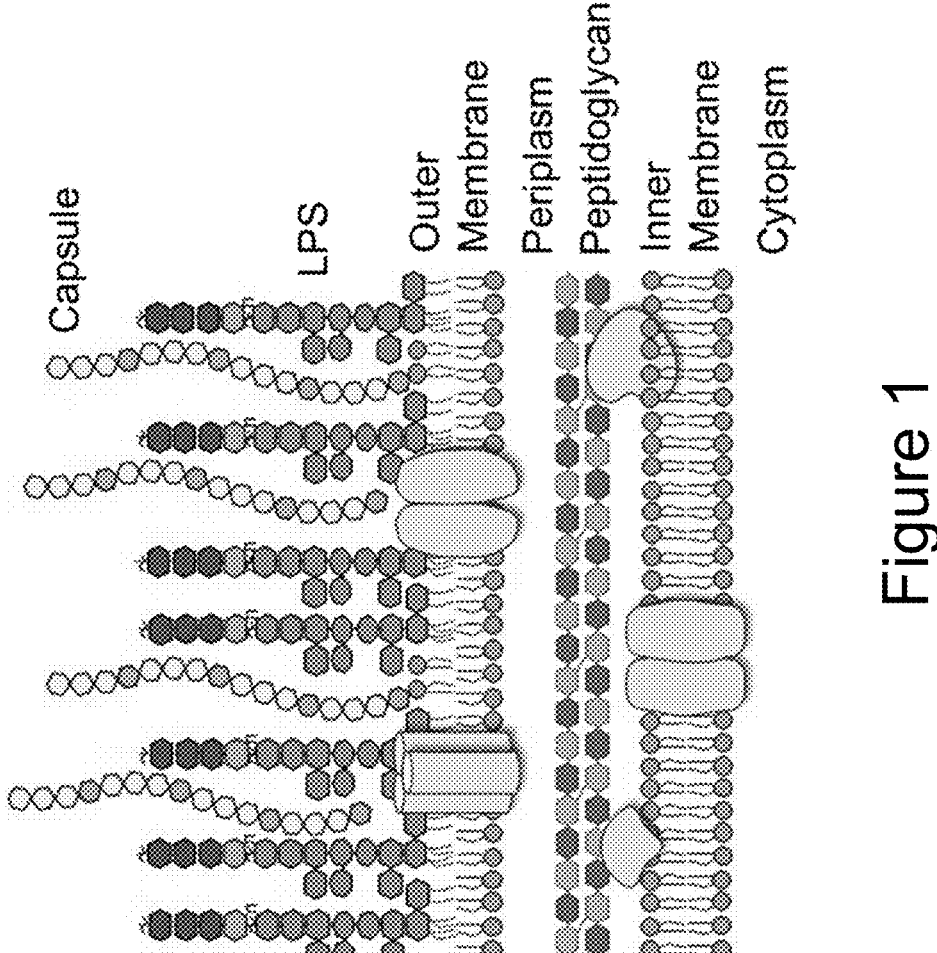
FIG. 1 depicts a schematic representation of a portion of *Pseudomonas aeruginosa*.
Figure 3:
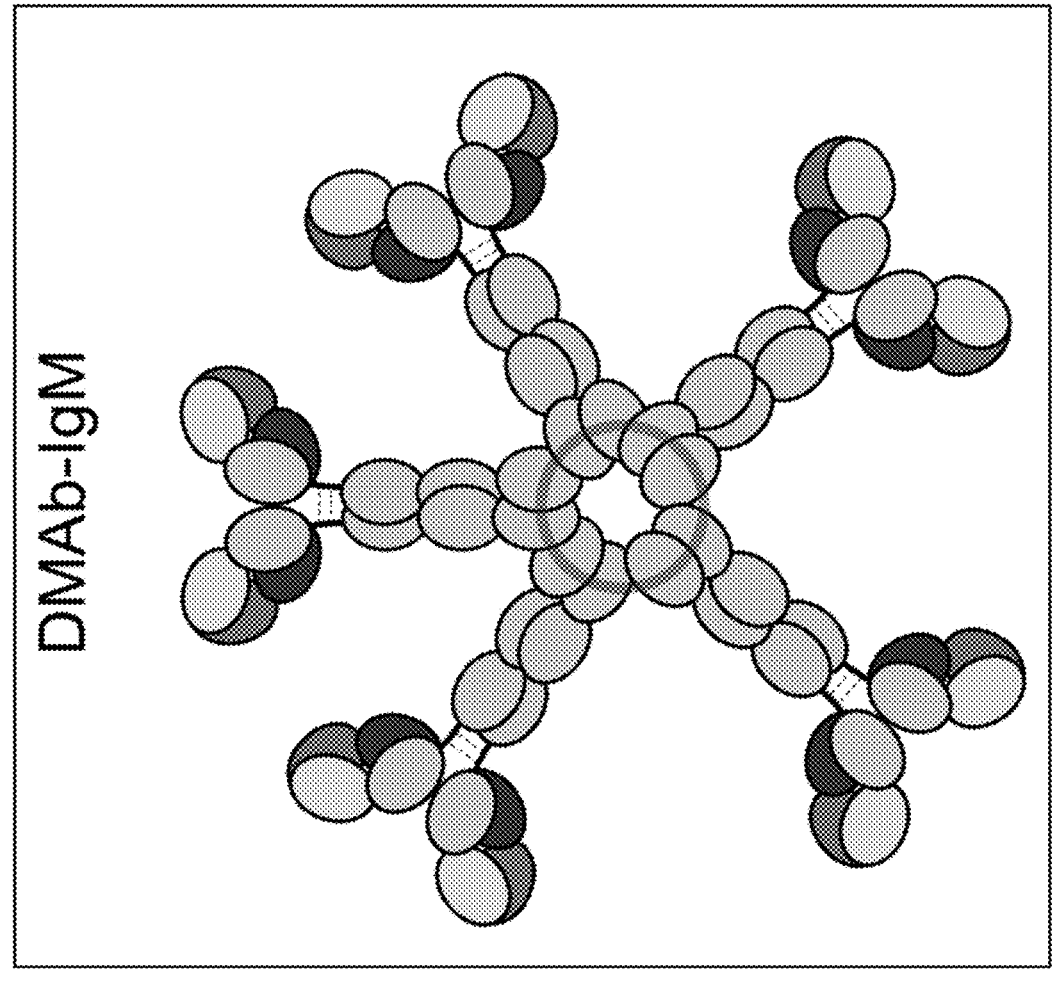
FIG. 3 depicts a schematic representation of DMAb-IgM.
Figures 4A, 4B:
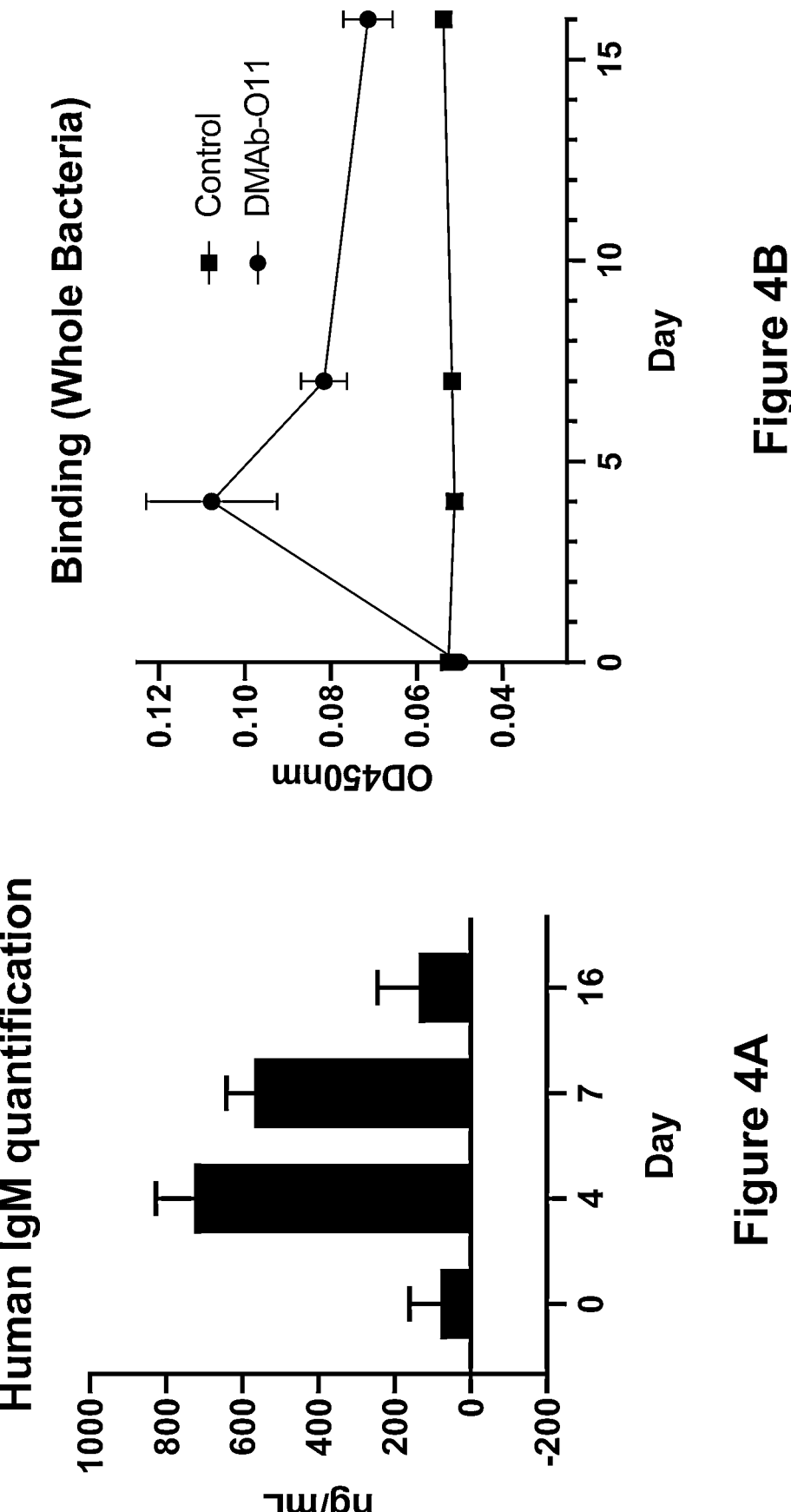
FIG. 4A and FIG. 4B, depicts exemplary results demonstrating that DMAb-O11 targets IATS O11 *Pseudomonas aeruginosa* via the analysis of in vivo expression in BALB/c mouse sera of human DMAb-O11. In vivo delivery of DMAb-O11—Panobac-O11-HC+Panobac-O11-LC+Human J-chain (150 ug total) was administered to transiently depleted BALB/c mice.

*Pseudomonas aeruginosa* serotype O11 accounts for 23% of nosocomial infections (FIG. 1 and FIG. 2). For this reason, the studies presented herein demonstrate the design and generation of anti-*Pseudomonas* "DNA monoclonal antibodies" (DMAb) based on panobacumab (Aerumab AR-101). DMAb nucleotide sequence were codon optimized, and optionally further comprise human J chain. Codon-optimized DMAbs were synthesized onto a human IgM1 constant domain (FIG. 3). Plasmid DNA encoding antibody was delivered to BALB/c mice (FIG. 4). In vivo expression in BALB/c mouse sera of human DMAb-O11 (DMAb-IgM; Panobac-O11-HC+Panobac-O11-LC+Human J-chain) demonstrated that DMAb-O11 (DMAb-IgM) targets IATS O11 *Pseudomonas aeruginosa*. Accordingly, efforts are directed toward ongoing DMAb-IgM sequence engineering to increase in vivo expression. This study supports DMAb as an alternative to existing biologic therapies.

DNA is a flexible platform to deliver genes and nucleotide sequences in vivo. DNA-encoded mAbs are protective against multi-drug resistant bacteria, with comparable efficacy to protein IgG mAb. DNA technology enables mAb delivery therapy for routine delivery and expands accessibility to the global market. The DMAbs can be combined with DNA vaccine technology to provide immediate and persistent immunity.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

---

What is claimed is:

1. A nucleic acid molecule encoding one or more synthetic antibodies or fragment thereof, wherein the nucleic acid molecule comprises at least one selected from the group consisting of:

a) a nucleotide sequence encoding a synthetic antibody, wherein the nucleotide sequence encodes an amino acid sequence that is at least about 80% identical to a sequence set forth in SEQ ID NO: 2 and an amino acid sequence that is at least about 80% identical to a sequence set forth in SEQ ID NO: 4;

b) a nucleotide sequence encoding a synthetic antibody, wherein the nucleotide sequence encodes an amino acid sequence that is at least about 80% identical to a sequence set forth in SEQ ID NO: 2, an amino acid sequence that is at least about 80% identical to a sequence set forth in SEQ ID NO: 4, and an amino acid sequence that is at least about 80% identical to a sequence set forth in SEQ ID NO: 6;

c) a nucleotide sequence encoding a fragment of a synthetic antibody, wherein the fragment of a synthetic antibody comprises a fragment of an amino acid sequence that is at least about 80% identical to SEQ ID NO:2 and a fragment of an amino acid sequence that is at least about 80% identical to SEQ ID NO:4; and d) a nucleotide sequence encoding a fragment of a synthetic antibody, wherein the fragment of a synthetic antibody comprises a fragment of an amino acid sequence that is at least about 80% identical to SEQ ID NO:2, a fragment of an amino acid sequence that is at least about 80% identical to SEQ ID NO:4, and a fragment of an amino acid sequence that is at least about 80% identical to SEQ ID NO: 6.

2. The nucleic acid molecule of claim 1, wherein the nucleotide sequence encodes a leader sequence.

3. The nucleic acid molecule of claim 1, wherein the nucleic acid molecule comprises an expression vector.

4. A composition comprising the nucleic acid molecule of claim 1.

* * * * *